(12) United States Patent
Harshman

(10) Patent No.: US 11,484,308 B2
(45) Date of Patent: Nov. 1, 2022

(54) METHODS AND DEVICES FOR FORMING A TISSUE FOLD

(71) Applicant: EndoGastric Solutions, Inc., Redmond, WA (US)

(72) Inventor: Scott Harshman, Kirkland, WA (US)

(73) Assignee: EndoGastric Solutions, Inc., Redmond, WA (US)

( * ) Notice: Subject to any disclaimer, the term of this patent is extended or adjusted under 35 U.S.C. 154(b) by 689 days.

(21) Appl. No.: 16/591,468

(22) Filed: Oct. 2, 2019

(65) Prior Publication Data

US 2020/0029965 A1 Jan. 30, 2020

Related U.S. Application Data

(62) Division of application No. 14/558,496, filed on Dec. 2, 2014, now Pat. No. 10,433,838, which is a division of application No. 12/383,109, filed on Mar. 18, 2009, now Pat. No. 8,906,037.

(51) Int. Cl.
| | | |
|---|---|---|
| *A61B 17/00* | (2006.01) | |
| *A61B 17/072* | (2006.01) | |
| *A61B 17/04* | (2006.01) | |
| *A61B 17/064* | (2006.01) | |
| *A61B 17/068* | (2006.01) | |
| *A61B 17/08* | (2006.01) | |

(52) U.S. Cl.
CPC ...... *A61B 17/072* (2013.01); *A61B 17/00234* (2013.01); *A61B 17/0401* (2013.01); *A61B 17/064* (2013.01); *A61B 17/068* (2013.01); *A61B 2017/00349* (2013.01); *A61B 2017/00818* (2013.01); *A61B 2017/00827* (2013.01); *A61B 2017/0409* (2013.01); *A61B 2017/0419* (2013.01); *A61B 2017/0464* (2013.01); *A61B 2017/0496* (2013.01); *A61B 2017/0649* (2013.01); *A61B 2017/07214* (2013.01); *A61B 2017/081* (2013.01)

(58) Field of Classification Search
CPC . A61B 17/00234; A61B 17/29; A61B 17/072; A61B 2017/00818; A61B 2017/00827; A61B 2017/2926; A61B 2017/00349
USPC .......................................... 606/139, 142, 143
See application file for complete search history.

*Primary Examiner* — Dianne Dornbusch
(74) *Attorney, Agent, or Firm* — Fulwider Patton LLP

(57) ABSTRACT

A device for forming a tissue fold includes a recess and an opening at the end of the recess. Tissue is drawn into the recess and through the opening using a tissue engaging element. As the tissue is drawn through the opening, the tissue layers are compressed together. A fastener is used to secure the tissue fold.

6 Claims, 4 Drawing Sheets

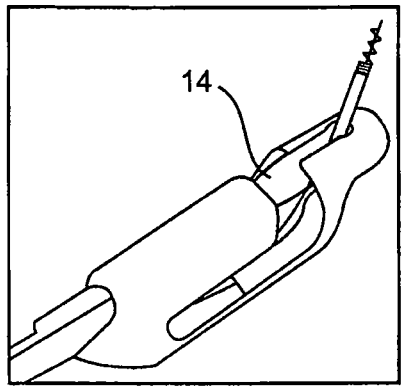 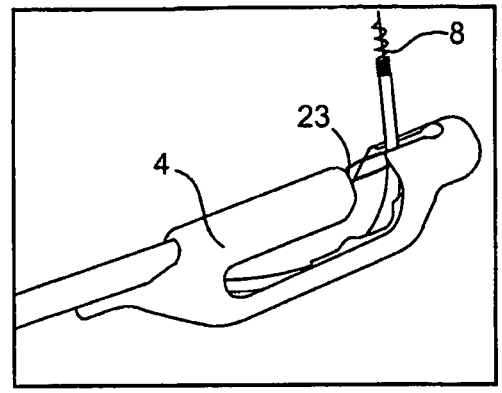
FIG. 4　　　　　　　　　FIG. 5
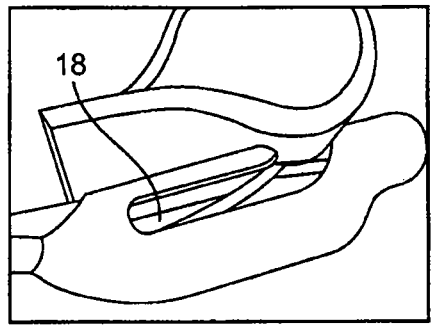 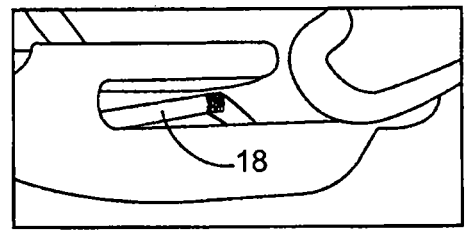
FIG. 6　　　　　　　　　FIG. 7
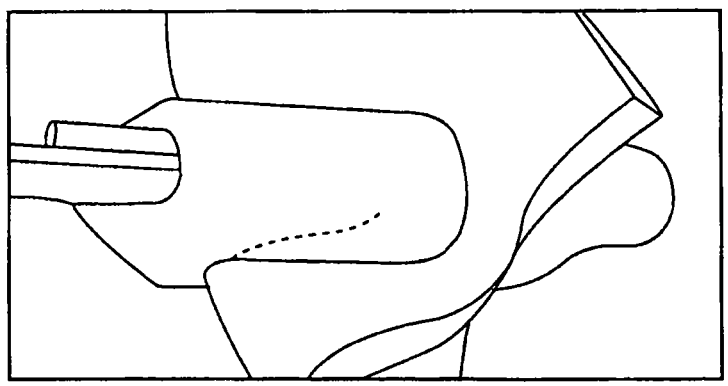
FIG. 8

METHODS AND DEVICES FOR FORMING A TISSUE FOLD

This application is division of U.S. Ser. No. 14/558,496 filed Dec. 2, 2014, which is a divisional application of U.S. Ser. No. 12/383,109 filed Mar. 18, 2009, now U.S. Pat. No. 8,906,037 issued Dec. 9, 2014, the entire contents of which are incorporated herein by reference.

BACKGROUND

The present invention is directed to methods and devices for approximating tissue and forming a tissue fold.

SUMMARY

The present invention provides a device for forming a tissue fold, which has a mold and a tissue engaging element. The mold has a recess and an opening leading to the recess. Tissue is drawn through the opening and into the mold using the tissue engaging element.

As tissue is drawn into the opening, the tissue forms a fold, which is compressed by the opening. In this manner, the entire fold is drawn through the opening and squeezed and compressed by the opening. The tissue layers are then fastened together to maintain tissue fold.

The opening is positioned at a distal end of the recess so that tissue is drawn proximally through the opening and into the tissue mold. The mold may also have two lateral openings, which communicate with the recess and with the opening at the distal end of the recess. The lateral edges of the tissue fold extend through the lateral openings as the tissue is drawn into the recess.

The tissue engaging element takes a curved path through the tissue mold and changes an angular orientation with respect to the mold by at least 45 degrees when passing through the mold.

The volume of the area around the device, such as the stomach, may also be reduced while drawing the tissue into the recess.

These and other aspects of the present invention will become apparent from the following description of the preferred embodiment.

DESCRIPTION OF DRAWINGS

FIG. 4 shows a tissue engaging element extending from a mold.

FIG. 5 shows the tissue engaging element positioned to engage tissue.

FIG. 6 shows the tissue engaging element engaged with tissue and the tissue drawn toward the mold.

FIG. 7 shows the tissue fold just before entering the mold.

FIG. 8 shows the tissue drawn into the recess and a fastener applied to maintain the tissue fold.

DESCRIPTION OF THE PREFERRED EMBODIMENTS

Figure 1:
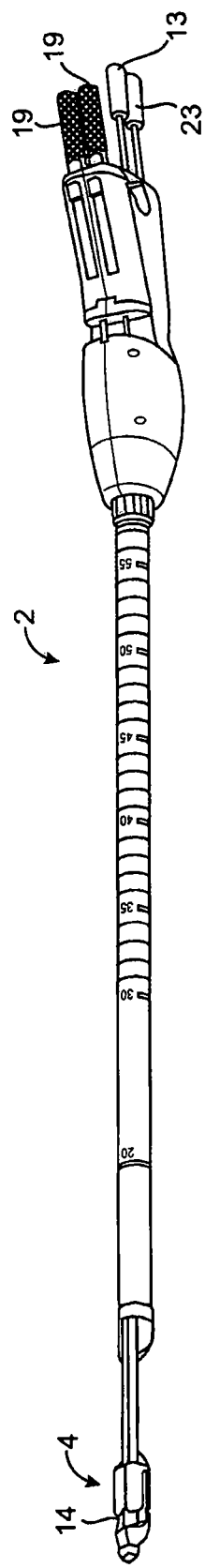
FIG. 1 shows a device for forming a tissue fold.
Figure 2:
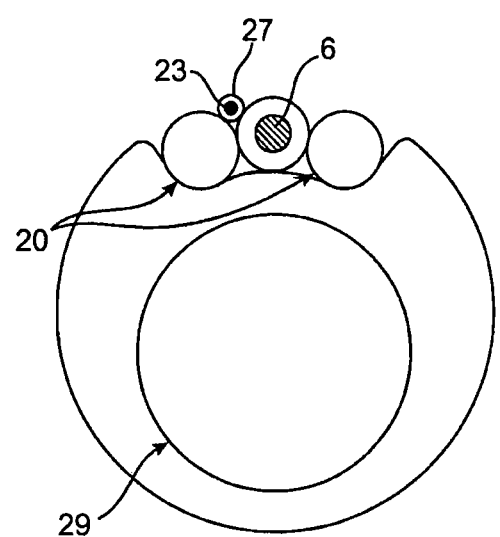
FIG. 2 shows a cross-sectional view of the device.
Figure 3:
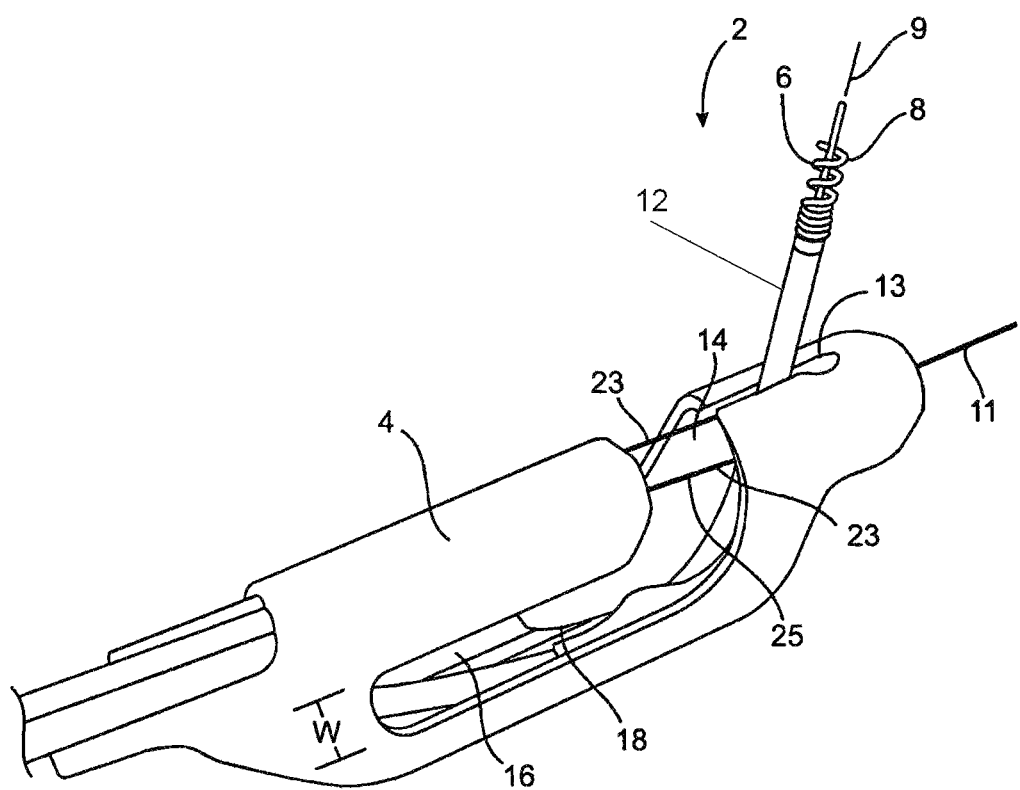
FIG. 3 shows a distal end of the device.

Referring to FIGS. 1-3, a device 2 for forming a tissue fold is shown. The device 2 has a tissue mold 4 and a tissue engaging element 6 which draws tissue into the mold 4.

The tissue engaging element 6 has a helical coil 8 with a sharp tip 10 which is rotated into engagement with tissue. The device 2 may include any other suitable mechanism for engaging tissue such as a hook, barb, or suction element. The tissue engaging element 6 is coupled to a cable 12 which may be rotated and translated in the manner described below to manipulate the element 6. The tissue engaging element 6 extends though a slot 13 in the body which stabilizes the element 6 and permit's the user to steer the element 6 with the mold 4. The coil 8 is initially directed somewhat laterally from the mold 4 as shown in FIG. 5. As the coil 8 moves into the mold 4, the coil 8 takes a curved path through the mold 4 so that a longitudinal axis 9 of the coil 8 changes angular orientation with respect to a longitudinal axis 11 of the mold by at least 45 degrees. A manipulator 13 extends from the proximal end of the device 2 and is used to move and rotate the coil 8. A lock (not shown) is used to lock rotation of the manipulator 13 (and coil 8) as described below in connection with the method of using the device 2.

The tissue mold 4 has an opening 14 which is relatively small so that the tissue fold is compressed and squeezed as the tissue enters the tissue mold 4. An advantage of the present invention is that squeezing the tissue in this manner may help to separate the tissue creating the fold from surrounding tissue. Such connections or adhesions to other tissue may not be desirable. An advantage of the present invention is that squeezing and compressing the tissue fold during introduction into the mold may help to reduce such connections and adhesions.

The tissue mold 4 has a recess 16 which receives the tissue fold. Two lateral openings 18 communicate with the recess 16 and with the opening 14. As the tissue is drawn into the mold 4, the lateral edges of the tissue fold extend through the openings 18 as shown in FIG. 8. The lateral openings 18 are generally L-shaped but may take any other suitable shape. The opening 14 leading to the recess 16 is at the distal end of the recess 16 so that the tissue is drawn proximally through the device 2. A width W of the lateral openings 14 may be relatively uniform over the length of the lateral openings 14 so that the lateral openings 14 can maintain a relatively uniform pressure on the tissue fold once the tissue enters the mold 4 and while it is drawn further into the recess 16.

One or more lumens 20 extends through the device 2 and are used to deliver one or more fasteners 22 to maintain the tissue fold (see FIGS. 2 and 8). The fastener 22 may be any suitable fastener and one such fastener 22 is described in U.S. Ser. No. 10/949,737, which is incorporated herein by reference. A proximal end 19 of the fastener extends from the device for manipulation by the user.

A centering mechanism 23 is also provided for centering and manipulating the tissue engaging element 6. The centering mechanism 23 may be a wire loop 25 which is looped around the element 6. The wire loop 25 may be tensioned to move the tissue engaging element 6 from the position of FIG. 4 to the position of FIG. 5 in which the element 6 is oriented substantially perpendicular to the longitudinal axis of the device 2. The wire loop 25 extends through a lumen 27 as shown in the cross-sectional view of FIG. 2. The tissue engaging element 6 is free to slide within the wire loop 25, however, the wire loop is not large enough to permit the coil to pass therethrough so that the wire loop 25 is eventually drawn back with the tissue engaging element 6.

Use of the device 2 is now described with reference to FIGS. 3-8. The following method relates to use in the stomach but the device 2 may find uses in other areas as well without departing from the scope of the invention. The device 2 is introduced down the patient's throat to the desired location for creating a tissue fold. An endoscope (not shown) is used to guide the device 2 to the desired location and is introduced through a lumen 29. The device 2 may pass through the endoscope or the two may extend side by side as is known in the art without departing from the scope of the invention. The centering mechanism 23 is then tensioned to move the element 6 to the position of FIG. 5 so that the coil 8 is perpendicular to the longitudinal axis of the mold. The helical coil 8 is then rotated into engagement with tissue. Once engaged with tissue, the coil 8 and tissue are permitted to return to their respective free states rotationally. The helical coil 8 is then locked against rotation in preparation for manipulating the tissue as described below.

The mold 4 is then oriented so that it will create a fold, which is aligned in the desired direction. The area around the device 2 may then be reduced in volume using vacuum. The lumen 20, lumen 29 or another independent lumen or device may be used to evacuate air from the area around the device 2. The helical coil 8 is then slowly drawn back into the mold 4 while the area around the device 2 is reduced in volume. As the tissue enters the mold 4, the tissue fold is compressed as it enters the opening 14 so that the entire fold is compressed and drawn through the relatively small opening 14. In this manner, tissue connections and adhesions on the far side of the tissue layers, which form the tissue fold may be released prior to forming the fold.

The coil 8 is then moved proximally to draw the tissue through the opening 14 and into the recess 16. As the coil 8 continues to draw the tissue into the recess 16, the lateral edges of the tissue extend through the lateral openings 18. One or more of the fasteners 22 are then deployed through the lumen 20 to secure the tissue fold.

The present invention has been described with respect to a preferred embodiment, however, it is understood that numerous modifications and alterations could be made without departing from the scope of the invention. For example, the lateral openings could be linear rather than curved and the fastener may be an adhesive rather than a mechanical fastener.

What is claimed is:

1. A method for forming a tissue fold, comprising:
   providing a stationary mold having a fixed volume recess and an opening leading to the recess and an elongated slot having a distal end and a proximal end, the proximal end of the elongated slot being adjacent to a distal end of the recess;
   moving a cable having a helical coil at a distal end of the cable outside the fixed volume recess by extending through the elongated slot located distally of the opening leading to the fixed volume recess and engaging tissue and drawing tissue through the opening and into the fixed volume recess;
   disposing a centering mechanism in the slot and looping the centering mechanism around the cable to move the cable to a position substantially perpendicular to a longitudinal axis of the stationary mold; and
   sizing the opening so that tissue drawn through the opening by the helical coil is compressed as the tissue fold enters the tissue mold.

2. The method of claim 1, further comprising:
   fastening together the tissue fold contained within the fixed volume recess with a fastener.

3. The method of claim 1, wherein:
   the opening is at a distal end of the fixed volume recess; and
   drawing the tissue proximally into the tissue mold using the helical coil.

4. The method of claim 1, wherein:
   changing the angular orientation of the cable and the helical coil with respect to a longitudinal axis of the tissue mold by at least 45 degrees when the cable and helical coil are moved through the mold.

5. The method of claim 1, wherein the centering mechanism is a wire loop wrapped around the cable.

6. The method of claim 5, wherein the cable freely slides through the wire loop, but the helical coil is larger than the wire loop and will not pass therethrough.

* * * * *